(12) United States Patent
Ahner et al.

(10) Patent No.: US 9,784,688 B2
(45) Date of Patent: Oct. 10, 2017

(54) APPARATUS FOR UNIFORMLY IRRADIATING AND IMAGING AN ARTICLE

(71) Applicant: Seagate Technology LLC, Cupertino, CA (US)

(72) Inventors: Joachim Walter Ahner, Livermore, CA (US); David M. Tung, Livermore, CA (US); Samuel Kah Hean Wong, Johor Bahru (MY); Henry Luis Lott, Fremont, CA (US); Stephen Keith McLaurin, Livermore, CA (US); Maissarath Nassirou, Fremont, CA (US); Florin Zavaliche, San Ramon, CA (US)

(73) Assignee: Seagate Technology LLC, Cupertino, CA (US)

( * ) Notice: Subject to any disclaimer, the term of this patent is extended or adjusted under 35 U.S.C. 154(b) by 589 days.

(21) Appl. No.: 14/046,648

(22) Filed: Oct. 4, 2013

(65) Prior Publication Data

US 2014/0098217 A1  Apr. 10, 2014

Related U.S. Application Data

(60) Provisional application No. 61/712,186, filed on Oct. 10, 2012.

(51) Int. Cl.
*G01N 21/88* (2006.01)
*H04N 7/18* (2006.01)
*G01N 21/95* (2006.01)

(52) U.S. Cl.
CPC ........... *G01N 21/8806* (2013.01); *H04N 7/18* (2013.01); *G01N 21/9501* (2013.01); *G01N 2201/0636* (2013.01)

(58) Field of Classification Search
CPC .............. G01N 21/88; G01N 21/9501; G01N 21/8806; G01N 2201/0636; H04N 7/18
(Continued)

(56) References Cited

U.S. PATENT DOCUMENTS 5,283,684 A * 2/1994 Thomas ............. G02B 21/0032
359/234
5,764,874 A * 6/1998 White ................. G01N 21/8806
355/67
(Continued)

FOREIGN PATENT DOCUMENTS

CN      1516143 A    7/2004
CN    102467924 A    5/2012
(Continued)

OTHER PUBLICATIONS

Weapon Industry Science and Technology Dictionary-Optical Engineering, National Defense Industry Press, p. 8-102 (May 31, 1993), translation.
(Continued)

*Primary Examiner* — Jay Patel
*Assistant Examiner* — Marine Matt

(57) ABSTRACT

Provided herein is an apparatus, including a reflective surface configured to reflect photons onto a surface of an article, a stage configured to support the article, and an assembly. The assembly is configured to radiate photons through the article to the reflective surface. The assembly is further configured to image the article with irradiance of the photons.

13 Claims, 6 Drawing Sheets

(58) Field of Classification Search
USPC .................................................... 348/87, 96
See application file for complete search history.

(56) References Cited

U.S. PATENT DOCUMENTS

| | | | | |
|---|---|---|---|---|
| 5,898,499 | A * | 4/1999 | Pressesky | G01N 21/88 |
| | | | | 356/237.2 |
| 6,252,242 | B1 * | 6/2001 | Brunfeld | G01N 21/9506 |
| | | | | 250/559.45 |
| 6,272,095 | B1 * | 8/2001 | Liu | G11B 7/0045 |
| | | | | 369/103 |
| 6,766,958 | B1 * | 7/2004 | Roh | G03H 1/0402 |
| | | | | 235/489 |
| 8,087,799 | B2 | 1/2012 | Hahn et al. | |
| 8,154,975 | B1 * | 4/2012 | Wang | G11B 7/14 |
| | | | | 369/103 |
| 8,319,960 | B2 | 11/2012 | Aiko et al. | |
| 8,363,214 | B2 | 1/2013 | Watanabe | |
| 2004/0008603 | A1 * | 1/2004 | Saitoh | G11B 7/139 |
| | | | | 369/99 |
| 2007/0258085 | A1 | 11/2007 | Robbins et al. | |
| 2009/0257058 | A1 | 10/2009 | Urano et al. | |
| 2009/0290168 | A1 | 11/2009 | Hamamatsu et al. | |
| 2012/0127843 | A1 * | 5/2012 | Wang | G11B 7/0065 |
| | | | | 369/53.12 |
| 2012/0133928 | A1 | 5/2012 | Urano et al. | |
| 2013/0201561 | A1 * | 8/2013 | McCluney | F21S 11/00 |
| | | | | 359/597 |

FOREIGN PATENT DOCUMENTS

| | | | | |
|---|---|---|---|---|
| JP | S58-11838 | A | 1/1983 | |
| JP | H05149885 | A | 6/1993 | |
| JP | 2003-161703 | A | 6/2003 | |
| JP | 2003-178493 | A | 6/2003 | |
| JP | 2003-329606 | A | 11/2003 | |
| JP | 2004-334158 | A | 11/2004 | |
| WO | WO 9810268 | A1 * | 3/1998 | ............. G01B 11/30 |
| WO | WO 9959917 | A1 | 11/1999 | |
| WO | 2009021207 | | 2/2009 | |
| WO | WO 2012051625 | A2 * | 4/2012 | ............. F21S 11/00 |

OTHER PUBLICATIONS

CN 1st Office Action dated Jul. 17, 2015 in CN Application No. 201310753599.1, Includes English Translation. 17 pages.
CN 2nd Office Action dated Mar. 11, 2016 in CN Application No. 201310753599.1, Includes English Translation. 13 pages.
CN 3rd Office Action dated Sep. 21, 2016 in CN Application No. 201310753599.1, Includes English Translation. 22 pages.

* cited by examiner

APPARATUS FOR UNIFORMLY IRRADIATING AND IMAGING AN ARTICLE

RELATED APPLICATIONS

This application claims the benefit of U.S. Provisional Patent Application No. 61/712,186, filed Oct. 10, 2012, by Ahner et al.

SUMMARY

Provided herein is an apparatus, including a reflective surface configured to reflect photons onto a surface of an article, a stage configured to support the article, and an assembly. In some embodiments, the assembly is configured to radiate photons through the article to the reflective surface. The assembly is further configured to image the article with irradiance of the photons.

These and other features and aspects of the inventive concepts may be better understood with reference to the following drawings, description, and appended claims.

DRAWINGS

DESCRIPTION

Figure 1:
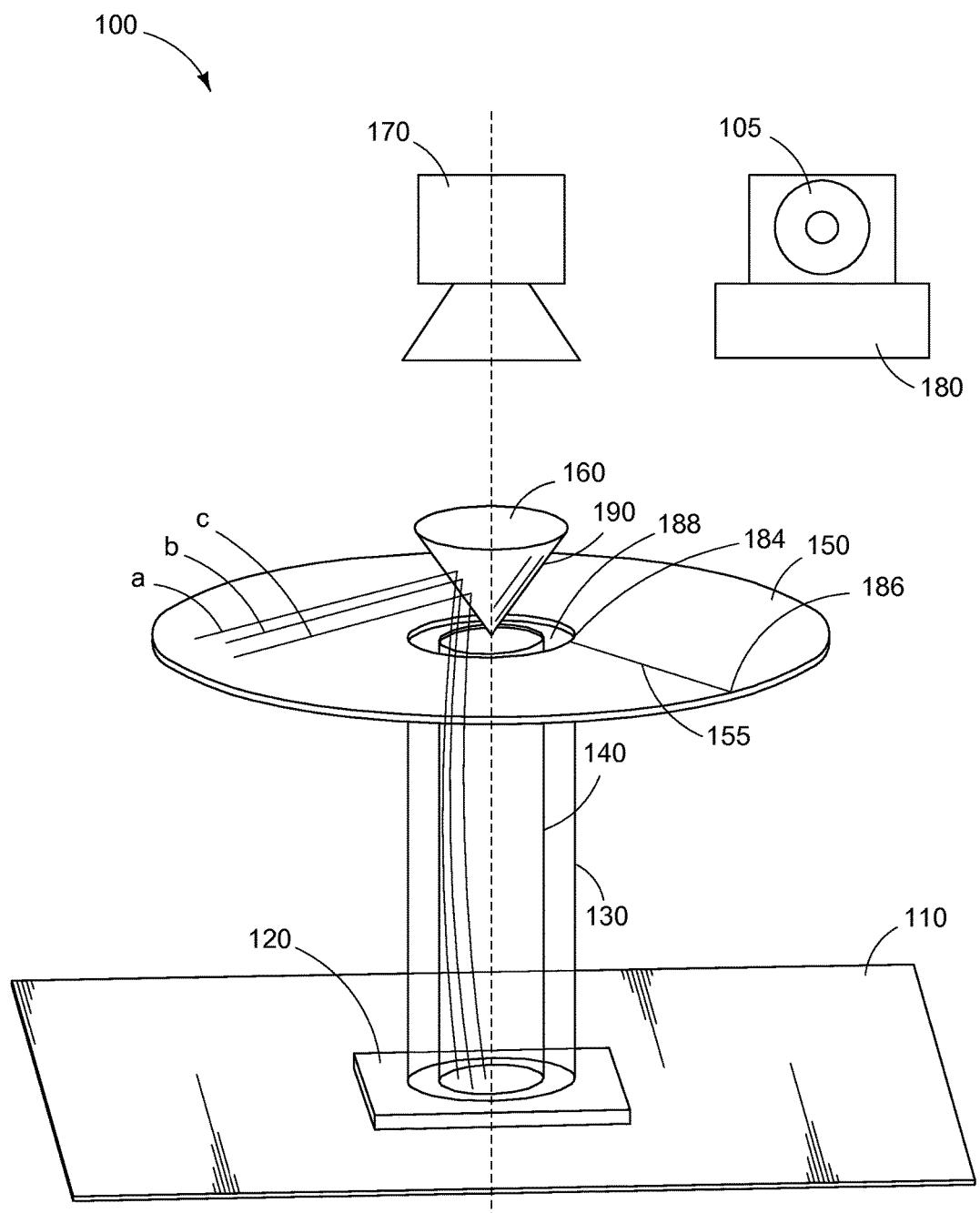
FIG. 1 shows an apparatus configured to produce an image of a uniformly irradiated article in accordance with an embodiment.

Before various embodiments are described in greater detail, it should be understood by persons having ordinary skill in the art that the embodiments are not limiting, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing the inventive concepts, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the embodiments thereof. For example, "first," "second," and "third" elements or steps need not necessarily appear in that order, and the embodiments thereof need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art to which the embodiments pertain.

An article fabricated on a production line may be inspected for certain features, including defects, such as particle and stain contamination, scratches and voids, that might degrade the performance of the article or a system including the article. For example, a final inspection may be performed on an optically smooth hard disk for microroughness, defects, such as pits or bumps, and/or contamination.

In some instances, defect detection and inspection may be performed by imaging the article with a camera. In order to discriminate among different types of features, the article is properly illuminated by a photon emitter. However, a photon emitter that is positioned above an article may cause reflected light and/or stray light to be captured by the camera and hinder the ability to detect certain features and defects. Further, depending on the angle and position of the photon emitter with respect to the article, the amount of photon irradiance on the article may be unevenly distributed, which may also cause certain features and defects to remain undetected. As such, provided herein are apparatuses configured to image an article with substantially uniform irradiance, and an arrangement to manage reflected light and stray light.

In some embodiments described herein, an apparatus is configured to position an article for imaging in between (1) a photon emitter and (2) a reflective surface and a camera. In such an arrangement, an article with uniform irradiance may be imaged without detecting reflected photons, reflected light, stray photons and/or stray light, thereby resulting in greater detectability and inspection of different types of features and defects. For example, a high-powered light source may project light through a center of a hard disk onto a conical mirror, which reflects the projected light onto a surface of the hard disk. In this example, by projecting light from the light source onto the conical mirror, rather than directly onto the surface of the hard disk, the angle and curvature of the conical mirror is used to manage stray light and light reflected from the surface of the disk. Specifically, the conical mirror may be configured with certain angle and curvature that prevents stray light and light reflected from the surface to be detected and recorded by a camera. In this way, image-based inspection is improved by generating images with greater detail and clarity of features of an article that are substantially unobstructed by stray and reflected light from the surface of an article (e.g., hard disks, reflective surfaces, media, sputtered surfaces, etc.).

In some embodiments, the apparatus may include a lens to transmit photons from a photon emitter to a reflective surface in order to image a uniformly irradiated article. The lens may be configured to redistribute photons received from the photon emitter, such that the lens monotonically increases a flux of photons as photons are projected across a surface of the article from an initial location to a final location of the surface of the article. In this way, the entire surface of the article is uniformly (or substantially uniformly) irradiated.

In an illustrative example, an apparatus configured to image a circular disk may include a lens that transmits light from a light source through a center of the disk and onto a conical mirror, which reflects the light onto the surface of the disk. In this example, in order to uniformly illuminate the surface of the disk, the lens increases the flux of light as light is projected across the surface of the disk from an inner circumference to an outer circumference of the disk. In other words, the lens redistributes the flux of light by increasing the flux of light as the annular surface area of the disk increases with the radius of the disk. It is appreciated that in order to have the same light power per unit area (e.g., uniform illumination, uniform irradiance) across the surface of the disk, the flux of light is increased to account for the change in radius as the light is projected onto the surface of the disk. As the example illustrates, the lens accounts for the changes in the radius of the disk by redistributing the flux of light.

In some embodiments, an apparatus described herein may image a uniformly irradiated article by projecting photons onto different locations of the article and subsequently recording images of the article. Then, the apparatus generates a composite image from the recorded images of a uniformly irradiated article. For instance, the apparatus may include a projector that projects a photon shaped form, such as a ring or a dot (e.g., a small photon spot), onto a surface of an article over a specific or predetermined interval. The photon form may be projected on an initial location of the article then moved across the article to a final location on the surface location over the specific interval. In this scenario, a camera may be configured to record images of the article as the photon form is moved across the article. The apparatus may then further generate a composite image based on the recorded images of an article that is uniformly irradiated. In this way, the apparatus described herein provides a mechanism to generate an image of a uniformly irradiated article by projecting photons over a period of time, rather than in a single instance.

FIG. 1 shows an apparatus configured to produce an image 105 of a uniformly irradiated article in accordance with an embodiment. The apparatus 100 includes, but is not limited to, a stage 110 supporting a photon emitter 120, a cylindrical stage 130 including a lens 140 and further supports an article 150, a reflective surface 160, a camera 170, and a computer 180. It is appreciated that the apparatus described herein is exemplary and is not intended to limit the scope of the inventive concepts.

In some embodiments, the apparatus 100 may be configured to generate an image of a uniformly irradiated article. For instance, the photon emitter 120 may project photons to lens 140. The lens 140 transmits the photons to the reflective surface 160. In some instances, described in greater detail in FIG. 2, the lens 140 redistributes the photon flux received from the photon emitter 120 by monotonically increasing the photon flux relative to a length, such as the radius 155, of the article 150. By increasing the photon flux relative to a length of the article 150, a uniform or a homogenous amount of photon power per unit area (e.g., uniform irradiance, uniform illumination) of the article may be achieved. Once the photon flux is transmitted from the lens 140 onto the reflective surface 160, the reflective surface 160 reflects the photons flux onto the surface of the article 150. Then, camera 170 images the article and the image is stored and recorded by computer 180.

Before proceeding to further describe the various components of apparatus 100, it is appreciated that article 150 as described herein may be, but not limited to, semiconductor wafers, magnetic recording media (e.g., hard disks for hard disk drives), and workpieces thereof in any stage of manufacture.

Referring now to stage 110, in some embodiments, the stage 110 supports the photon emitter 120. In some embodiments, the stage 110 may be a piezoelectric controlled stage, such as atomic force microscopy ("AFM") stage. The stage 110 may be a housing for one or components, in some instances. For example, the stage 110 may house a power source, fiber optic cables for the photon emitter 120, and/or wave and/or polarization filters to use in conjunction with photon emitter 120.

Apparatus 100 further includes a photon emitter 120 supported by stage 110 and positioned near lens 140 to emit and project photons onto lens 140. In some instances, the photon emitter 120 may be a high powered light source, such as for example a solid state light source and/or a laser. In some embodiments, the photon emitter 120 may emit white light, blue light, UV light, infrared, coherent light, incoherent light, polarized light, non-polarized light, or some combination thereof. It is appreciated that the types of light discussed are merely examples, and are not intended to limit the scope of the concepts described herein. In some embodiments, the photon emitter 120 or a light source may emit any type of photons that may be used to illuminate and image article 150.

Referring now to cylindrical stage 130, the cylindrical stage 130 is positioned over the photon emitter 120 and houses lens 140. Further, cylindrical stage 130 supports article 150 to allow article 150 to be positioned in between the photon emitter 120 or a light source and the lens 140 and the reflective mirror 160. In some instance, the cylindrical stage may support article 150 in another position, such as first, second or some third position that allows article 150 to be uniformly irradiated. In some embodiments, cylindrical stage 130 may include a hastening or clamping system (not shown) to secure article 150. For example, the cylindrical stage 130 may include clamps near the inner radius 184 of article 150. In one example, the cylindrical stage 130 may include clamps near the outer radius 186. In some instances, the cylindrical stage 130 may be a transparent stage as illustrated in FIG. 1. In some instances, the cylindrical stage may be an opaque stage.

Although FIG. 1 illustrates a cylindrical stage, it is intended as example and is not intended to limit the scope of the concepts described herein. In some embodiments, instead of a cylindrical stage, a rectangular prism shaped stage, a triangular prism shaped stage, or a stage configured to support an article in between (1) a photon emitter and/or a light source and/or a lens and (2) a reflective surface.

Apparatus 100 also includes a lens 140. Lens 140 is configured to transmit photons from the photon emitter 120 to the reflective surface 160. For instance, lens 140 transmits photons from the photon emitter 120 to the reflective surface 160 through article 150. In some embodiments, the lens 140 is configured to redistribute photons received from the photon emitter 120, such that article 150 is uniformly irradiated. For instance, lens 140 may be configured to receive a photon flux from the photon emitter 150 and redistribute the photon flux, such that the lens 140 monotonically increases the photon flux projected upon the surface of article 150 as the annular surface area of the article 150 increases with the radius 155. In other words, the lens increases the photons flux as photons are projected across the surface 182 of the article 150 from an initial location 184 (e.g., inner diameter) to a final location (e.g., outer diameter) in order to achieve the same photon power per unit area (e.g., uniform irradiance) across the surface of article 150, which is described in greater detail in FIG. 2.

In some embodiments, lens 140 may be a gradient-index ("GRIN") lens of a certain index of refraction profile, an objective lens, or a combination of a GRIN and objective lenses. It is appreciated that the lens described herein are exemplary, and are not intended to limit the scope of the concepts described herein. Lens 140 may be a lens configured to transmit photons and change the photon flux in a manner that allows an article, such as article 150, to be uniformly irradiated.

Lens 140, as illustrated in FIG. 1, is housed within cylindrical stage 130. The diameter of lens 140, in some instances, may be the same or similar to the diameter of the base of the reflective surface 160. In some instance, the diameter of lens 140 may range from a diameter that is the same as the base of the diameter of reflective surface 160 to a diameter that is the same or similar as the diameter of the center hole 188 of article 150. It is appreciated that the diameters described herein are some illustrative examples, and are not intended to limit the scope of the concepts described herein. In some instances, the diameter of lens 140 may be configured in a manner to uniformly irradiate the surface of article 150.

Although FIG. 1 illustrates a single lens, it is merely an example and is not intended to limit the scope of the concepts described herein. In some instances, more than one lens may be used to transmit photons from a photon emitter to a reflective surface. It is further appreciated that the illustration of lens 140 being aligned with the photon emitter 120, the reflective surface 160 and camera 170 is intended to be an illustrative example, and is not intended to limit the scope of the concepts described herein. In some embodiments, the lens 140 may be positioned off-center, at an angle, or positioned in a manner that allows the lens to transmit photons from the photon emitter 150 to reflective surface 160 to uniformly irradiate the surface of article 150.

Apparatus 100 includes a reflective surface 160 positioned over the article 150. The reflective surface 160 receives photons from lens 140 through the center hole 188 of the article 150, and reflects the photos onto the surface of article 150, as illustrated as photon rays a, b, and c. The reflective surface 160, as illustrated in FIG. 1, is a conical mirror. In some embodiments, instead of a conical mirror, the reflective surface 160 may be a parabolic mirror, a concave mirror, a convex mirror, and/or a reflective surface that is configured to reflect photons onto a surface of an article. In some embodiments, the curvature 190 of the reflective surface 160 may be configured to be substantially linear or non-linear based on index profile of lens 140, which is described in greater detail in FIGS. 2 and 3.

In some embodiments, apparatus 100 includes a camera 170. In some embodiments, camera 170 may be communicatively coupled to computer 180. In some embodiments, camera 170 may be configured to record images of a uniformly irradiated article 150 and transmit the recorded images to computer 180 for storage and feature analysis. In some embodiments, the camera 110 may be a complementary metal-oxide semiconductor ("CMOS") camera, a scientific complementary metal-oxide semiconductor ("sCMOS") camera, a charge-coupled device ("CCD") camera, or a camera configured for use in feature detection and identification. Although FIG. 1 illustrates a single camera, it is intended to be exemplary and is not intended to limit the scope of the embodiments. In some embodiments, the apparatus 100 may include a plurality of cameras configured record images of an article.

Further, apparatus 100 includes a computer 180. In some embodiments, the computer 180 may be communicatively coupled to camera 170 to store images of article 150 recorded by camera 170. The computer 180 generates a composite image of a substantially uniformly irradiated article based on the recorded images of the article, in some embodiments. In some embodiments, the computer 170 may be communicatively coupled to the photon emitter 120 to cause the photon emitter 120 to emit photons according to a predetermined schedule. In some instances, the computer 180 may signal the photon emitter 120 to emit a predetermined photon flux onto lens 140. In some embodiments, the computer 170 may be further configured to identify features of article 150, such as disk defects. It is appreciated that computer 180 may be a desktop computer, a workstation, a portable device (e.g., a mobile device, a tablet, a laptop, or a smartphone), or some computing device that may be configured to store images.

Figure 2:
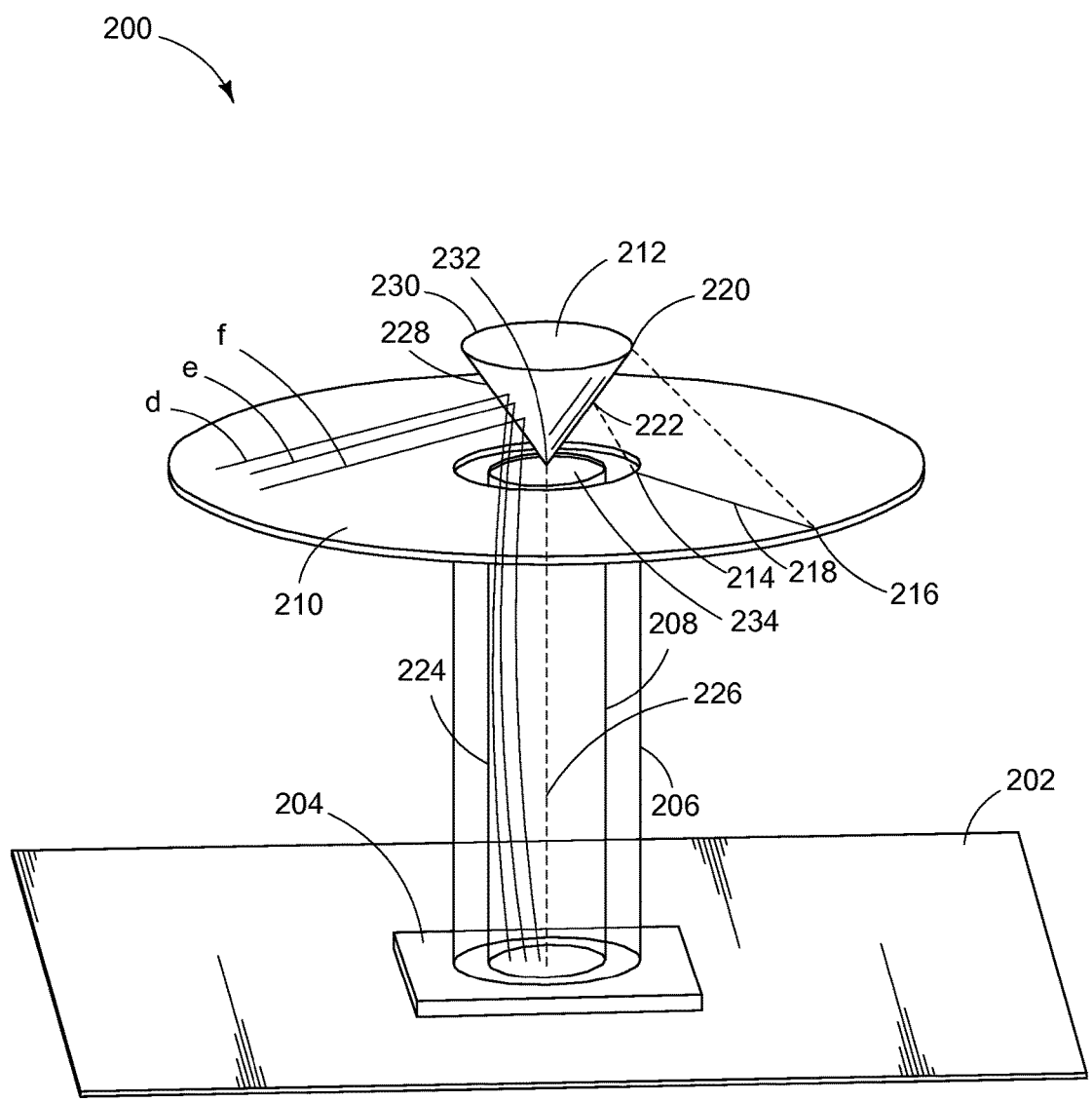
FIG. 2 shows an assembly configured to uniformly irradiate an article in accordance with an embodiment.

Referring now to FIG. 2, an assembly configured to uniformly irradiate an article is shown in accordance with an embodiment. Assembly 200 includes, but is not limited to, a stage 202, a photon emitter 204, a cylindrical stage 206 supporting article 210, a lens 208, and a conical mirror 212. In some embodiments, stage 202, photon emitter 204, cylindrical stage 206, lens 208 and conical mirror 212 may be substantially similar to the stage 110, photon emitter 120, cylindrical stage 130, lens 140 and reflective surface 160, respectively, as described in FIG. 1. In some embodiments, assembly 200 may be a part of an apparatus, such as apparatus 100 of FIG. 1.

In some embodiments, photon emitter 204 emits a flux of photons onto lens 208. Then, lens 208 redistributes the flux of photons received from the photon emitter 204 by monotonically increasing the flux of photons such that photons are projected across the surface of article 210 from an initial surface location (e.g., inner radius 214) to a final surface location (e.g., outer radius 216) along a length (e.g., radius 218 of article 210) with uniform irradiance/illumination. By increasing the photon flux as the photons are projected along a length of the article 210, a uniform or a homogenous amount of photon power per unit area (e.g., uniform irradiance, uniform illumination) of the article may be achieved. Once photons are transmitted from the lens 208 onto the conical mirror 212, the conical mirror 212 reflects the photons onto the surface of article 210.

As noted above, in order to achieve uniform irradiance across the surface of article 210, lens 208 redistributes the photons of a certain photon flux received from the photon emitter 204 by monotonically increasing the flux of photons as photons are projected across the surface of the article from an initial location (e.g., inner radius 214) to a final location (e.g., outer radius 216) on the surface of article along a length (e.g., radius 214) of article 210. For example, lens 212 redistributes the photon flux received from photon emitter 204 to project a greater flux of photons onto a surface location of the reflective surface (e.g., location 220) corresponding to the outer diameter 216 in comparison to a flux of photons projected onto a surface location of the reflective surface (e.g., location 222) corresponding to the inner diameter 214. In this way, by increasing the photon flux as photons are projected radially outward along radius 218, the article is uniformly irradiated.

It is appreciated that the photon flux is redistributed to compensate for the relative distance of a surface location of an article from a light source and/or a photon source. That is, with respect to FIG. 2, as the distance increases from the inner diameter 214 to the outer diameter 216 relative to the conical mirror 212, which reflects the photons received from lens 208, the photon flux (e.g., the number of photons per unit time) is increased to compensate for the distance between a surface location of the article and the conical mirror. It is appreciated if the same photon flux is projected across the surface of article 210, the irradiance of article decreases as photons are projected from the inner radius 214 to the outer radius 216. As such, by redistributing the photon flux as described herein to account for the relative distance of a surface location to a photon and/or light source, a uniformly irradiated article may be achieved.

As described above, lens 208 is configured to redistribute the photon flux of photons received from the photon emitter 204 by monotonically increasing the photon flux relative to a length (e.g., radius 218) of article 210. In some embodiments, this is achieved based on the index of refraction profile of lens 208. For instance, lens 208 may be a GRIN lens that may have a certain index of refraction profile such that a greater amount of photons are redirected toward the outer radius 224 of lens 208 in comparison to the center 226 of the lens, as illustrated by photon rays d, e and f. In this way, the photon flux projected out near or at radius 224 of lens 208 is greater in comparison to the photon flux projected out near or at the center 226 of lens 208, thereby resulting in greater photon flux projected on the surface near the outer radius 216 of article 210 in comparison the photon flux on the surface near the inner radius 214 of article 210. It is appreciated that the illustrations of rays d, e and f are exemplary, and it is further appreciated that lens 208 may transmit more than three photon rays from the photon emitter 204 to the conical mirror 212.

Figure 3:
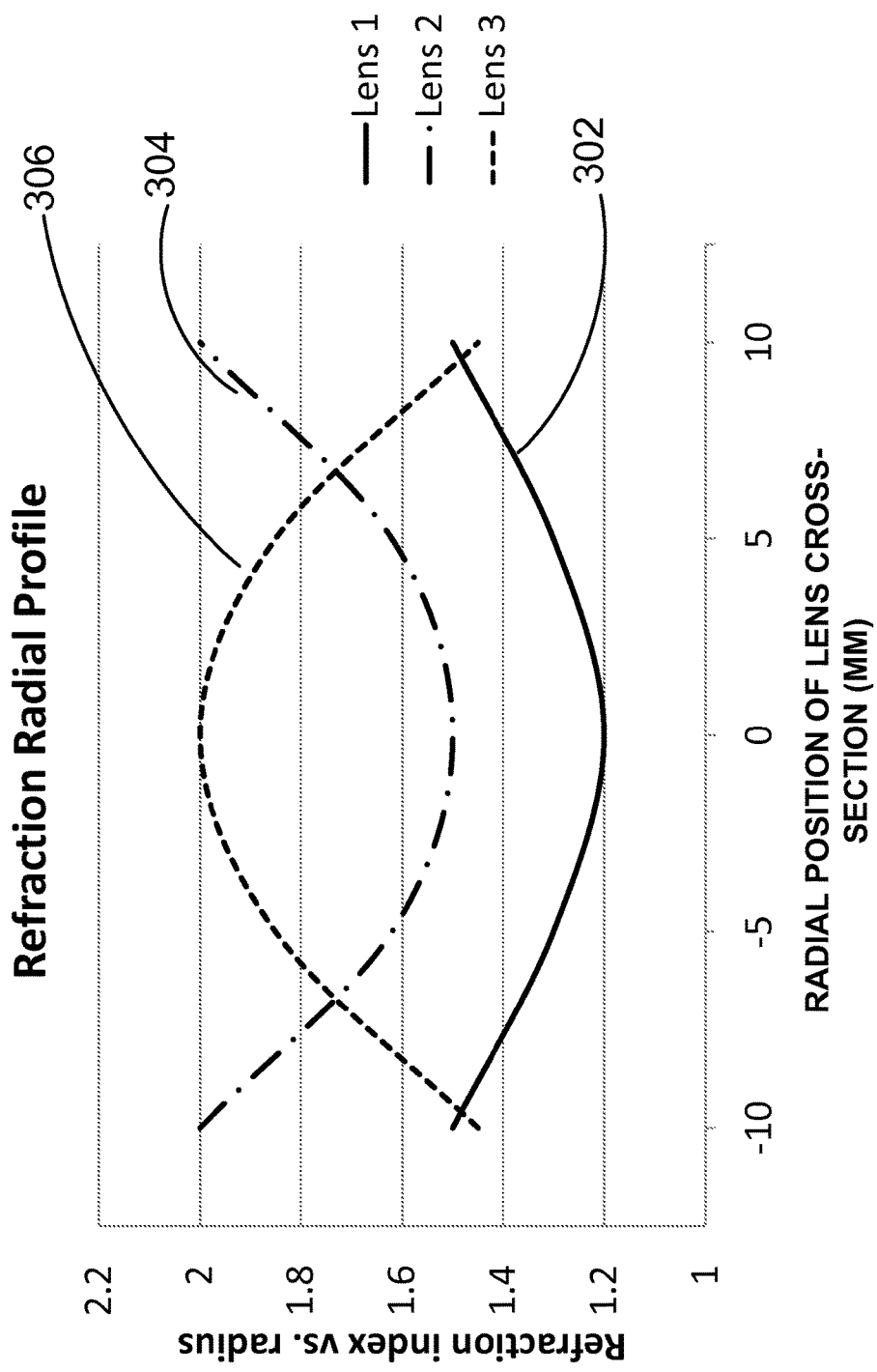
FIG. 3 shows index of refraction profiles of lenses in accordance with some embodiments.

Briefly turning to FIG. 3, index of refraction profiles of lenses is shown in accordance with some embodiments. In some embodiments, lenses 140 and 208 of FIGS. 1 and 2, respectively may be configured with the index of refraction profiles described herein.

FIG. 3 provides a plot of a refractive index as a function of a radius in a lens according to an embodiment. For example, a lens, as described herein, may have a refractive index of about 1.5 at an outer radius (e.g., outer radius 224 of FIG. 2) of the lens and refractive index of about 1.2 near the center of the lens (e.g., center 226 of FIG. 2), as illustrated in plot 302 (e.g., Lens 1). In one example, a lens, as described herein, may have a refractive index of about 2 near or at an outer radius of the lens and a refractive index of about 1.5 near the center of the lens, as illustrated in plot 304 (e.g., Lens 2). In some instances, a lens, as described herein, may have reflective index of about 1.5 near the outer radius of the lens and refractive index of about 2 near the center of the lens, as illustrated in plot 306 (e.g., Lens 3).

It is appreciated that the refraction index profiles described in FIG. 3 are merely examples, and that different lenses with different index of refraction profiles may be used to affect the imaging of a uniformly irradiated article. Further, it is appreciated that the index of refraction profile of a lens may be based on material used to form the lens. In some instances, a lens as described herein may be made of a homogenous material or a combination of materials. For example, a lens, as described herein, may include of materials such as, optical glasses, plastics, germanium, zinc selenide, sodium choloride, and/or some combination thereof.

Returning to FIG. 2, as discussed above, the refraction index profile of lens 208 may be used to effect the imaging of a uniformly irradiated article by redistributing the photon flux as described herein. After the lens 208 transmits the photons onto the conical mirror 212, the conical mirror 212 reflects the photons onto the surface of article 210.

Although FIG. 2 illustrates a conical mirror 212 with a linear surface 228 angled from a base 230 to apex 232, it is intended to be an example and is not intended to limit the scope of the concepts described herein. In some embodiments, the surface 228 of conical mirror 212 may be a non-linear surface, such a convex or concave surface.

In some embodiments, the curvature of surface 228 of conical mirror 212 may be based on the refraction index profile of lens 208. It is appreciated that as photons exit from the surface 234 of lens 210, the photons may be incident on the conical mirror 212 at a certain angle (e.g., incident angle) due to the refraction index profile of lens 208. As such, the photons may be further incident at a certain angle on the surface of article 210. To ensure that the incident angle of the photons on the surface of article 210 is at an angle that prevents reflected photons and/or stray photons/lights from being detected by a camera (not shown) used to image article 210, the curvature of the surface 228 of conical mirror 212 may be selected such that photons are directed at a certain desired incident angle on the surface of article 210. For example, the curvature of surface 228 of conical mirror 212 may be adjusted to be linear or non-linear to cause photons to be incident at a 90° angle. In some examples, the curvature of surface 228 of conical mirror 212 may be adjusted to cause photons to be incident on the surface at an angle ranging from 0° to 180°, inclusive.

In some embodiments, the curvature of surface 228 of conical mirror 212 may be further based on the surface curvature of article 210. In some embodiments, the surface 228 of conical mirror 212 may remain a linear surface as illustrated in FIG. 2, and instead, the surface 234 of lens 208 may be a convex or a concave surface to affect the incidence angle of photons on the surface of article 210. In some instances, lens 208 may be a combination of lenses, such as GRIN lens to adjust the photon flux and an optical lens to adjust the incident angle of photons on the surface of article 210. For example, the lenses may be arranged such that the GRIN lens receives photons from a photon emitter at one end and transmits the photons to an optical lens at the other end. In this example, the optical lens, then, further transmits to photons to a reflective surface, such as conical mirror 212. In some embodiments, the curvature of surface 228 of conical mirror 212 and/or the curvature of surface 234 of lens 208 may be linear and/or non-linear. By adjusting the curvatures of surface 228 of conical mirror 212 and/or of surface 234 of lens 208, the photon reflection and/or stray photons/light from the surface of article 210 may be managed, thereby resulting in greater visibility and detections of features of article 210.

Although FIG. 2 illustrates a conical mirror 212, it is intended to be an example and is not intended to limit the scope of the concepts described herein. In some embodiments, instead of a conical mirror, a parabolic mirror or a reflective mirror as described in FIG. 1 may be used. Further, as FIG. 2 illustrates, assembly 200 provides a mechanism to uniformly irradiate an article and further manage reflected photons and stray photons/light from the surface of an article, which allows for better images of an article for feature detection and inspection.

Figure 4:
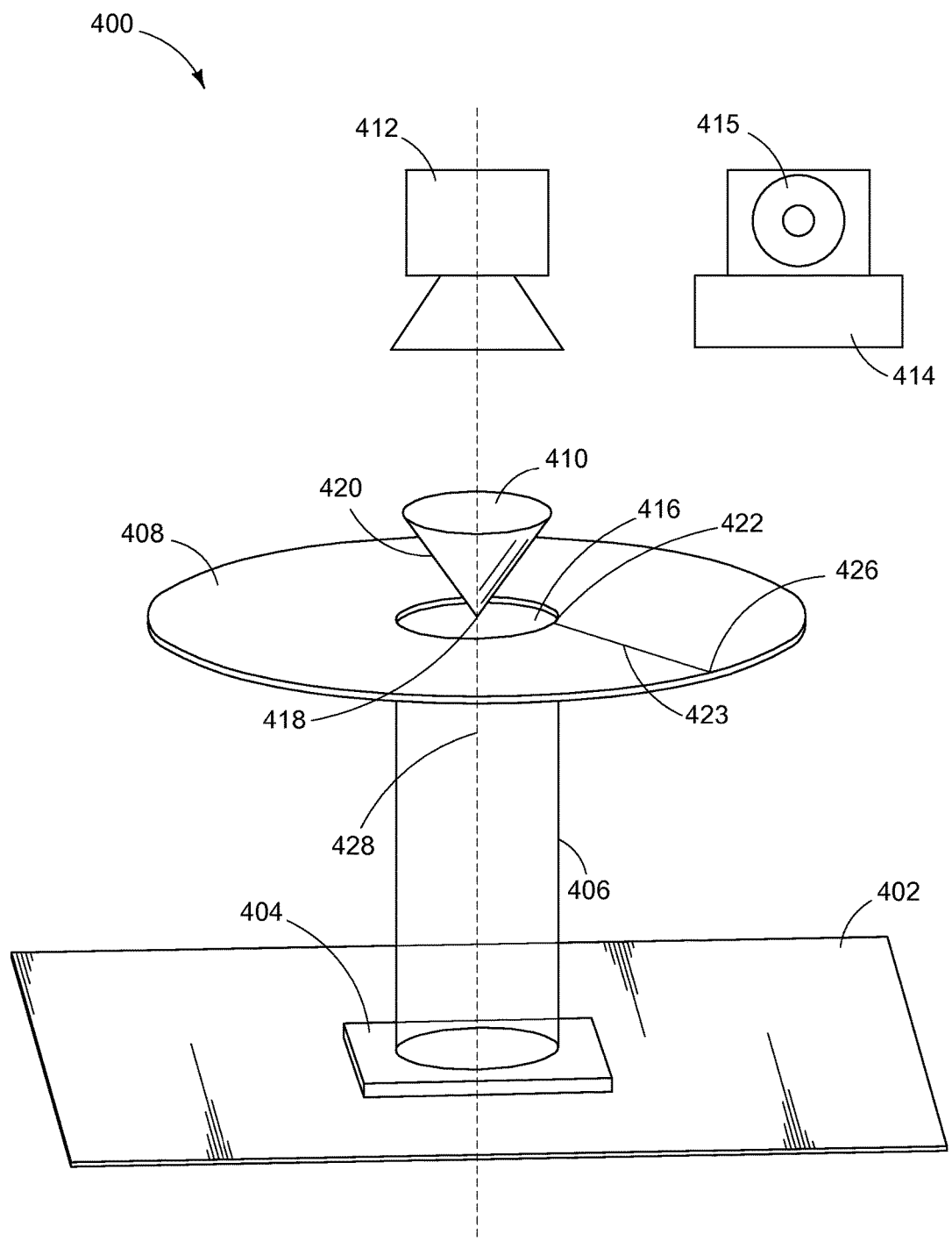
FIG. 4 shows an apparatus configured to produce an image of a uniformly irradiated article by projecting photons on the article over a time interval in accordance with an embodiment.

Referring now to FIG. 4, an apparatus configured to produce an image of a uniformly irradiated article by projecting photons on the article over a time interval is shown in accordance with an embodiment. The apparatus 400 includes, but is not limited to, a stage 402 that supports a projector 404, a cylindrical stage 406 supporting an article 408, a reflective surface 410, a camera 412, and a computer 414. In some embodiments, apparatus 400 is substantially similar to apparatus 100 of FIG. 1, except that apparatus 400 includes a projector 404. For example, stage 402, cylindrical stage 406, article 408, reflective surface 410, camera 412 and computer 414 may be substantially similar to stage 110, cylindrical stage 130, article 150, reflective surface 160, camera 170 and computer 180 of FIG. 1, respectively.

In some embodiments, apparatus 400 may be configured to generate an image 415 of a uniformly irradiated article by projecting a photon based form onto a surface of the article over a time interval. For instance, projector 404 may project a photon shaped form, such as a photon shaped ring or a photon shaped dot. Camera 412, in some instances, records one or more images of the article over the time interval as the reflective surface 410 reflects the photon form onto the surface of the article 408. Then, computer 414 generates a composite image of a uniformly irradiated article based on the recorded images.

In some embodiments, the projector 404 is aligned with the camera 412 and the reflective surface 410, and further supported by stage 402. As noted above, such an arrangement allows for the management of reflected photons and/or stray photons/light. In some embodiments, projector 404 includes a photon emitter (not shown) to emit photons. In some instances, the photon emitter of projector 404 may be substantially similar to photon emitter 120 of FIG. 1. In some instances, the photon emitter of projector 404 may be a metal-halide lamp, one or more light-emitting diodes ("LEDs"), and/or a laser.

In some embodiments, the projector 404 may be configured to emit photon of a certain photon shaped form, such as photon shaped rings, photon shaped dots, photon shaped strips, photon shaped stars, photon shaped squares, photon shaped circles, photon shaped rectangles and/or some user and/or system selected photon shaped form. In some instances, projector 404 may be a digital light processing ("DLP") projector including a digital micromirror device ("DMD") that may manipulate the shape of the photons emitted from the projector into a specific photon form (e.g., a ring, a dot) as described in greater detail below. In some instances, projector 404 may be an analog projector that may be manually manipulated to project a photon form as described herein.

In order to generate an image of a uniformly irradiated article, projector 404 projects a photon form across a surface of the article 408. For instance, the projector 404 projects a photon form to an initial location on the surface of the article 408, and, over a time interval, the projector 404 moves the photon form across the surface of the article 408 to a final location. As the photon form moves across the surface of article 408, camera 412 images the article and transmits the images to computer 414. Then, computer 414 generates a composite image of a uniformly irradiated article based on the images recorded by camera 412. In some embodiments, the predetermined time interval may range from a microsecond to minutes. For example, the time interval may be 1 second, 2 seconds, 3 seconds, 10 seconds, 30 seconds, 1 minute, 2 minutes, 5 minutes, 10 minutes, and/or 15 minutes. The time interval to project a photon form may be some arbitrary time period and/or a user and/or system defined time interval, in some instances.

Figure 5:
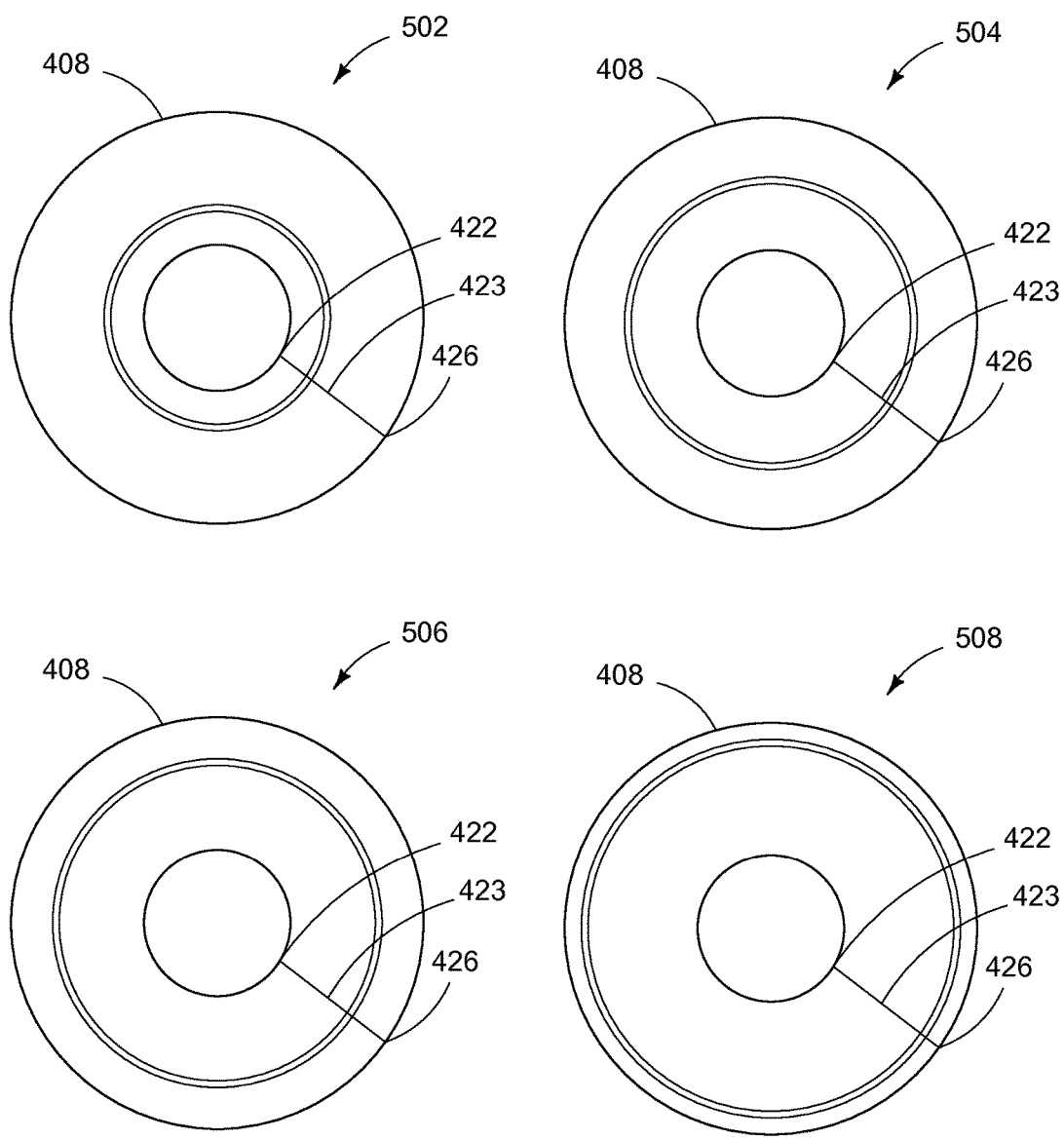
FIG. 5 illustrates an eagle eye-view perspective of a photon based form projected on a surface of an article in accordance with an embodiment.

In an illustrative example, in order to generate a composite image of uniformly irradiated article, projector 404 may be used to project a photon shaped ring across the surface of article 408. Initially, projector 404 projects a photon shaped ring through the center hole 416 onto the reflective surface 410, which is illustrated as a conical mirror in FIG. 4. It is noted that the reflective surface 410 may be referred interchangeably as a conical mirror or a reflective surface. In this example, the projector 404 projects the photon shaped ring near apex 418 of the conical mirror 410. The conical mirror 410, then, reflects the photon shaped ring near an inner radius 422 of article 408, as illustrated in 502 of FIG. 5, which illustrates an eagle eye-view perspective of the photon shaped ring projected onto the surface of article 408. In a similar manner, the projector 404 subsequently moves the photon shaped ring onto different locations of the conical mirror 410 from the apex 418 to the base 420 to radially move the photon shaped ring along radius 423 of article 408, as illustrated in 504-508 of FIG. 5.

In this example, in order to image a uniformly irradiated article, sub-time intervals of the predetermined time interval is increased as the photon shaped ring moves radially outward from the inner radius 422 to the outer radius 426. More specifically, if a time interval to project photon shaped ring across the surface of article 408 is 1 second, then the sub-time intervals of 1 second increases as the photon shaped ring moves from the initial location (e.g., inner radius 422) to the a final location (e.g., outer radius 426). That is, with reference to FIG. 5, the photon shaped ring projected on article 408 as illustrated in 502 may be projected for a sub-time interval of 1 microsecond (μs), whereas photon shaped ring projected in 504, 506, and 508 may be projected for 2 μs, 4 μs, 8 μs, respectively. It is appreciated that as the photon shaped ring moves radially outward along the radius 423 toward the outer diameter 426, the photon shaped ring is projected for longer time intervals to increase the amount of photon flux exposed onto the surface of the article 408 in order achieve the same irradiance at each location a photon shaped ring is projected. For instance, in FIG. 5, the irradiance of the photon shaped rings illustrated 502-508 are the same.

It is further appreciated that the discussion of a time interval of 1 second and sub-intervals of 1 μs, 2 μs, 4 μs, 8 μs are illustrative, and are not intended to limit the scope of the concepts described herein. For instance, the time interval and sub-time intervals may range from μs to minutes, or any other user and/or system defined time and sub-time intervals. For example, the time interval may be 1 second, 2 seconds, 3 seconds, 10 seconds, 30 seconds, 1 minute, 2 minutes, 5 minutes, 10 minutes, and/or 15 minutes. The sub-time intervals may be 1 to 10 or 20-50 nanoseconds, 1-30 μs, 1-30 seconds, and/or 1-10 minutes, in some examples. It is further appreciated that the illustration in FIG. 5 of projecting a photon ring at four different locations are illustrative, and are not intended to limit the scope of the concepts described herein. For instance, the photon ring may have been projected onto to a plurality of locations of the article. For example, the photon ring may have been projected onto as few as two different locations to as many as thousands of different locations on the surface of the article.

It also appreciated that the discussion that the projector 402 moves the photon shaped ring from the apex 418 to the base 420 to project the photon shaped ring from an inner radius 422 to an outer radius 426 is illustrative, and is not intended to limit the scope of the concepts described herein. For instance, the projector 402 may move a photon shaped ring from the base 420 to the apex 418. As such, the projector 404 initially projects the photon shaped ring at the outer radius 426, and then, projects the photon shaped ring across the article to the inner radius 412. In such a scenario, projector 402 may decrease the sub-time intervals to expose a location with a photon shaped ring as the photon shaped ring is moved across the article 408 from the outer radius 426 to the inner radius 422.

Figure 6:
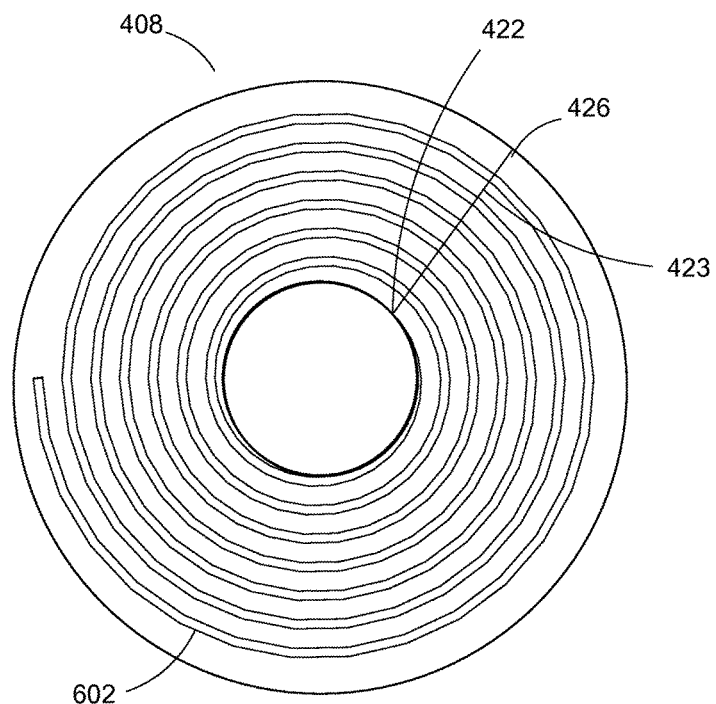
FIG. 6 illustrates an eagle eye-view perspective of a photon based form projected on a surface of an article in accordance with an embodiment.

In another illustrative example, in order to generate a composite image of uniformly irradiated article, projector 404 may be used to project a photon shaped spot and/or dot across the surface of article 408 over a predetermined time interval. Similar to projecting a photon shaped ring as discussed above, projector 404, initially, projects a photon shaped dot at or near apex 418 of the conical mirror 410. Then, the projector 404 subsequently projects the photon shaped dot onto different locations of the conical mirror 410 by processing the photon shaped along the central axis 428. In this way, when the conical mirror 410 reflects the photon shaped dot onto the surface of article 408 over the predetermined time interval, the photons are projected as a spiral from the center of the article 408 to the outer radius 426 of the article 408, as illustrated in FIG. 6. FIG. 6 illustrates an eagle eye-view perspective of photon shaped dot projected as a spiral on the surface of article 408 over the predetermined time period.

In this example, in order to image a uniformly irradiated article, the projector 404 projects the photon shaped dot at a speed (e.g., velocity) that decreases as the photon shaped dot is moved in an outward spiral from the inner diameter 422 to the outer diameter 426. For instance, the speed may gradually change following a K/r radial velocity profile where r is the radius (e.g, radius 423) and K is a constant rate at which the speed to project the photon shaped dot is changed. As an example, the photon shaped dot moves radially outward along radius 423 over a 1 second time interval and the movement of the photon shaped slows down by K/r. In one example, the speed may change gradually following a −K*r+r0 where r0 is the initial radius (e.g., inner diameter 422) and −K is the linear rate of speed change. It is appreciated that the −K suggests that the speed at which the photon shaped dot is emitted on the surface of article 408 slows down as the photon shaped dot moves further outward from the inner diameter 422 to the outer diameter 426. It is appreciated that by decreasing the speed of the photon shaped dot, the amount of photon flux exposed on the surface of the article increases as the photon moves radially outward along radius 423. In this way, the same photon irradiance is incident at each surface location of article 408 that the photon shaped dot is projected upon because the increase in the photon flux compensates for the increase in the radial length of article 408 as the photon shaped dot moves along the radius 423 to the outer diameter 426. For example, spiral 602 of FIG. 6 has a substantially uniform irradiance from the inner radius 422 to the outer radius 426.

It appreciated that the discussion of the projector 402 moving the photon shaped dot from apex 418 to base 420 to project a photon shaped dot from an inner radius 422 to an outer radius 426 is illustrative, and is not intended to limit the scope of the concepts described herein. For instance, the projector 402 may move a photon shaped dot from the base 420 to the apex 418. As such, the projector 404 initially projects the photon shaped dot at the outer radius 426, and then, projects the photon shaped dot across the article to the inner radius 422. In such a scenario, the projector 402 may increase the speed a photon shaped dot is moved across the article 408 from the outer radius 426 to the inner radius 422.

Although the examples discussed above describe a projector projecting a photon shaped form in the shape of a ring or a dot, it is appreciated that photon shaped forms discussed are illustrative and is not intended to limit the scope of the concepts described herein. As noted above, the projector 422 may be configured to project other photon shaped forms, such as a star, a square, a triangle, a rectangle, or some other user and/or system defined photon shaped form. Further, it is appreciated that the illustration of a conical mirror 410 of FIG. 4 is illustrative, and is not intended to limit the scope of the concepts described herein. In some embodiments, apparatus 400 may include a reflective surface as described in FIG. 1, such as a parabolic mirror, instead of a conical mirror.

Referring now to camera 412, in some embodiments, camera 412 records one or more images of the article 408 over the predetermined time as the photon shaped form is iteratively projected onto the surface of article 408 from an initial location (e.g., inner radius 422) to a final location (e.g., outer radius 426). Then, camera 412 transmits the recorded images to computer 412.

In some embodiments, computer 414, based on the recorded images, generates a composite image of a uniformly irradiated article. In some instances, computer 414 may be programmed to time integrate the recorded images based on the predetermined time interval. In some implementations, computer 414 may be programmed to integrate the recorded images based on a velocity (e.g., speed) a photon shaped form was projected onto the surface of the article while the article was being imaged. In some embodiments, computer 414 may be further configured to perform feature detection and analysis by mapping features of article 408. For instance, computer 414 may be programmed to use pixel interpolation for further mapping of features and defects of article 408. Computer 414, in some embodiments, may be configured to cause the projector 404 to project photons shaped form of certain shapes, control the time interval to image the article, control the sub-time intervals to project a photon shaped form on different surface locations of article 408, and/or cause the projector to project a photon shaped form at different speeds as the photon shaped form is moved from one surface location to another surface location of article 408.

As such, provided herein is an apparatus, including a photon emitter configured to emit photons, a lens, a reflective surface, and a stage configured to support an article. In some embodiments, the stage is positioned in between the lens and the reflective surface. The lens is configured to receive photons from the photon emitter and is further configured to project the photons onto the reflective surface, in some embodiments. In some embodiments, the reflective surface is configured to receive the photons from the lens and reflect the photons onto a surface of the article with a substantially uniform irradiance of photons.

In some embodiments, the apparatus further includes a camera configured to image the surface of the article. In some embodiments, the camera is selected from the group consisting of a complementary metal-oxide semiconductor ("CMOS") camera, a scientific complementary metal-oxide semiconductor ("sCMOS") camera, and a charge-coupled device ("CCD") camera.

In some embodiments, the lens is configured to redistribute a flux of photons by monotonically increasing a flux of photons as photons are projected across the surface of the article from an initial location to a final location of the surface of the article. In some embodiments, the article is a disk including of an inner diameter and an outer diameter. The lens projects a greater flux of photons onto a surface location of the reflective surface corresponding to the outer diameter of the article in comparison to a flux of photons projected onto a surface location of the reflective surface corresponding to the inner diameter of the article, in some embodiments. In some embodiments, the lens is selected from the group consisting of a gradient index lens, an objective lens, and a combination of a gradient lens and an objective lens. In some embodiments, the reflective surface is a conical mirror or a parabolic mirror. The article further includes a center configured to allow a flux density of photons to be projected there through, in some embodiments.

Also provided herein is an apparatus, including a reflective surface configured to reflect photons onto a surface of an article; a stage configured to support the article; and an assembly configured to radiate photons through the article to the reflective surface. In some embodiments, the assembly is further configured to image the article with irradiance of the photons.

In some embodiments, the assembly is configured to project a flux of photons by monotonically increasing the flux of photons relative to a length of the article. The assembly includes a lens and a photon emitter, in some embodiments. In some embodiments, the assembly is configured to supply photons in a form onto the reflective surface.

In some embodiments, supplying the photon form includes supplying the photon form to an initial location on the surface of the article and moving the photon form across the surface of the article to a final location on the surface of the article over a time interval. In some embodiments, a speed of moving the photon form from an initial location on the surface of the article to a final location on the surface of the article lessens over the time interval. In some embodiments, the assembly includes a projector configured to supply the photons, a camera configured to record a plurality of images of the article over a time interval, and a computer configured to generate a composite image of the article from the plurality of images with a substantially uniform irradiance.

Further provided herein is an apparatus, including a projector configured to project photons in a photon form onto a reflective surface over a time interval. In some embodiments, the reflective surface is configured to reflect the photon form onto a surface of an article positioned between the reflective surface and the projector. The apparatus further a computer configured to generate a composite image of a substantially uniformly irradiated article based on recorded images of the article over the time interval as the reflective surface reflects the photon form onto a surface of the article, in some embodiments.

In some embodiments, the photon form is a ring or a dot. In some embodiments, the time interval is about 1 to 2 seconds. In some embodiments, the reflective surface is a conical mirror or a parabolic mirror.

In some embodiments, the projector is configured to project the photon form to an initial location on the surface of the article and move the photon form across the surface of the article to a final location on the surface of the article over the time interval. In some embodiments, the projector is further configured to increase a sub-time interval to project the photon form as the photon form moves from the initial location to the final location. In some embodiments, the projector is configured to move the photon form from an initial location on the surface of the article across the surface to a final location on the surface of the article at a speed that decreases as the photon form moves from the initial location to the final location.

While the embodiments have been described and/or illustrated by means of particular examples, and while these embodiments and/or examples have been described in considerable detail, it is not the intention of the applicant(s) to restrict or in any way limit the scope of the embodiments to such detail. Additional adaptations and/or modifications of the embodiments may readily appear to persons having ordinary skill in the art to which the embodiments pertain, and, in its broader aspects, the embodiments may encompass these adaptations and/or modifications. Accordingly, departures may be made from the foregoing embodiments and/or examples without departing from the scope of the embodiments, which scope is limited only by the following claims when appropriately construed.

What is claimed is:

1. An apparatus, comprising:
    a photon emitter configured to emit photons;
    a lens;
    a reflective surface;
    a stage configured to support an article, wherein
        the stage is positioned in between the photon emitter and the reflective surface,
        the lens is configured to receive the photons from the photon emitter and is further configured to project the photons through the article and onto the reflective surface, and
        the reflective surface is configured to receive the photons from the lens and reflect the photons onto a surface of the article with a substantially uniform irradiance of photons, based on an index of refraction profile of the lens; and
    a camera configured to image the surface of the article.

2. The apparatus of claim 1 wherein the camera is selected from the group consisting of a complementary metal-oxide semiconductor ("CMOS") camera, a scientific complementary metal-oxide semiconductor ("sCMOS") camera, and a charge-coupled device ("CCD") camera.

3. The apparatus of claim 1, wherein the lens is configured to redistribute a flux of photons by monotonically increasing a flux of photons as photons are projected across the surface of the article from an initial location to a final location of the surface of the article.

4. The apparatus of claim 1, wherein
    the article is a disk comprising of an inner diameter and an outer diameter, and
    the lens projects a greater flux of photons onto a surface location of the reflective surface corresponding to the outer diameter of the article in comparison to a flux of photons projected onto a surface location of the reflective surface corresponding to the inner diameter of the article.

5. The apparatus of claim 1, wherein the lens is selected from the group consisting of a gradient index lens, an objective lens, and a combination of a gradient lens and an objective lens.

6. The apparatus of claim 1, wherein the reflective surface is a conical mirror or a parabolic mirror.

7. The apparatus of claim 1, wherein the article further includes a center configured to allow a flux density of photons to be projected there through.

8. An apparatus, comprising:
a reflective surface configured to reflect photons onto a surface of an article;
a stage configured to support the article; and
an assembly configured to radiate the photons through the article to the reflective surface and then from the reflective surface to the surface of the article, wherein the assembly is further configured to image the article with irradiance of the photons,
the assembly is further configured to project a flux of photons by monotonically increasing the flux of photons relative to a length of the article, and
the flux of photons projected out near or at a radius of a lens is greater in comparison to the flux of photons projected out near or at a center of a lens.

9. The apparatus of claim 8, wherein the assembly comprises a lens and a photon emitter.

10. The apparatus of claim 8, wherein the assembly is configured to supply photons in a form onto the reflective surface.

11. The apparatus of claim 10, wherein supplying the photon form comprises supplying the photon form to an initial location on the surface of the article and moving the photon form across the surface of the article to a final location on the surface of the article over a time interval.

12. The apparatus of claim 10, wherein a speed of moving the photon form from an initial location on the surface of the article to a final location on the surface of the article lessens over the time interval.

13. The apparatus of claim 8, wherein the assembly comprises:
a projector configured to supply the photons;
a camera configured to record a plurality of images of the article over a time interval; and
a computer configured to generate a composite image of the article from the plurality of images with a substantially uniform irradiance.

* * * * *